US00PP26215P3

(12) United States Plant Patent
Nir

(10) Patent No.: US PP26,215 P3
(45) Date of Patent: Dec. 15, 2015

(54) *CHAMELAUCIUM* PLANT NAMED 'EARLY NIR'

(50) Latin Name: *Chamelaucium uncinatum*
Varietal Denomination: EARLY NIR

(71) Applicant: Nitzan Nir, Kfar Hess (IL)

(72) Inventor: Nitzan Nir, Kfar Hess (IL)

( * ) Notice: Subject to any disclaimer, the term of this patent is extended or adjusted under 35 U.S.C. 154(b) by 104 days.

(21) Appl. No.: 13/987,628

(22) Filed: Aug. 16, 2013

(65) Prior Publication Data

US 2015/0052646 P1 Feb. 19, 2015

(51) Int. Cl.
*A01H 5/02* (2006.01)

(52) U.S. Cl.
USPC ..... Plt./229
CPC ..... *A01H 5/02* (2013.01)

(58) Field of Classification Search
USPC ..... Plt./229
CPC ..... A01H 5/00; A01H 5/02
See application file for complete search history.

(56) References Cited

PUBLICATIONS

Macnish et al. Scientia Horticulturae 102(4): 415-432, 2004 (Abstract).*

* cited by examiner

*Primary Examiner* — Keith O. Robinson
(74) *Attorney, Agent, or Firm* — Cassandra Bright

(57) ABSTRACT

A new and distinct *Chamelaucium* cultivar named 'EARLY NIR' is disclosed, characterized by unique flower color, branch structure and early blooming. The new variety is a *Chamelaucium*, normally producing cut flower stems, or as a garden or container plant.

1 Drawing Sheet

Latin name of the genus and species: *Chamelaucium uncinatum.*

Variety denomination: 'EARLY NIR'.

BACKGROUND OF THE INVENTION

The new *Chamelaucium* cultivar is a product of open pollination by the inventor, Nitzan Nir, in Kfar Hess, Israel. The new variety was discovered as a seedling growing in a field of various *Chamelaucium uncinatum* varieties during February of 2010, at a commercial nursery in Kfar Hess, Israel. The breeder has identified the seed parent as *Chamelaucium* 'Della', unpatented. The pollen parent is unknown.

Asexual reproduction of the new cultivar has been performed by vegetative cuttings. This was first performed at a commercial nursery in Kfar Hess, Israel in April of 2010 and has shown that the unique features of this cultivar are stable and reproduced true to type in successive generations.

SUMMARY OF THE INVENTION

The cultivar 'EARLY NIR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EARLY NIR'. These characteristics in combination distinguish 'EARLY NIR' as a new and distinct *Chamelaucium* cultivar:

1. Clear pink flower color, with a darker center.
2. Unique branch structure.

3. Early blooming
4. High quantity of stems harvested per plant

PARENT COMPARISON

Plants of the new cultivar 'EARLY NIR' are similar to plants of the unpatented seed parent, *Chamelaucium* 'Della', in most horticultural characteristics, however, plants of the new cultivar 'EARLY NIR' produce a different flower color and date of bloom than the seed parent. Flowers of the new variety are darker pink than flowers of 'Della'. Additionally, flowers of the new variety have a dark Red-Purple hypanthium, whereas flowers of 'Della' have a pink hypanthium.

COMMERCIAL COMPARISON

Plants of the new cultivar 'EARLY NIR' are comparable to the variety *Chamelaucium* 'Nir', unpatented. The two *Chamelaucium* varieties are similar in most horticultural characteristics; however, the new variety 'EARLY NIR' has a different date of bloom and flower color than the comparator. Flowers of 'Nir' are white to light pink, with a red-purple hypanthium. Flowers of 'Early Nir' are medium pink with a red-purple hypanthium.

Plants of the new cultivar 'EARLY NIR' can also be compared to the commercial variety *Chamelaucium* 'M.B. Orchid', unpatented. These varieties are similar in most horticultural characteristics; however 'EARLY NIR' has a different bloom date than the comparator.

BRIEF DESCRIPTION OF THE PHOTOGRAPH

The accompanying photograph in FIG. 1 illustrates in full color a close up of typical flowers and foliage of 'EARLY NIR' at approximately 1 year of age. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'EARLY NIR' plants grown outdoors in Kfar Hess, Israel. The growing temperature ranged from 15° C. to 35° C. during the day and from −2° C. to 35° C. during the night. General light conditions are bright, normal sunlight. Measurements and numerical values represent averages of typical plant types. Chemical treatments included general fungicides and insecticides.

Botanical classification: *Chamelaucium uncinatum* 'EARLY NIR'.

Propagation

Time to produce a rooted plantlet: 30 to 60 days at approximately 24° C.

Root description: Fibrous.

Root color: Varies, new root growth near Orange 159D, older, woodier roots near Grey-Brown N 199A, 199A, 199B.

Plant

Age of plant described: A mature plant, at least 2 months old from a rooted cutting.

Growth habit: Upright.

Height: 200 cm to top of foliage. 197 cm to top of flowers.

Plant spread: 80 cm.

Growth rate: Rapid.

Branching characteristics: Easily forming lateral branches.

Length of primary lateral branches: 60 cm to 150 cm.

Diameter of lateral branches: 0.4 cm.

Quantity of primary lateral branches: 120-150 stems per season. These are the harvested flowering stems.

Characteristics of primary lateral branches:

- *Form*.—Round.
- *Diameter*.—0.5 cm.
- *Color*.—Near RHS Yellow-Green 147A.
- *Texture*.—Smooth.
- *Strength*.—Stems brittle.

Internode length: 2 to 8 cm.

Foliage

Leaf:

- *Arrangement*.—Opposite.
- *Quantity*.—Approximately 6 leaves, in the 10-15 cm section from the top of the branch.
- *Average length*.—2.5 cm.
- *Average width*.—0.1 cm.
- *Shape of blade*.—Needle.
- *Apex*.—Acute.
- *Base*.—Attenuate.
- *Margin*.—Entire.
- *Texture of surfaces*.—All surfaces glabrous.
- *Pubescence*.—None.
- *Aspect*.—Straight, approximately 45 degree angle from stem.
- *Color*.—Young foliage: Near RHS Yellow-Green 147B. Mature foliage: Near RHS Green 137A.
- *Venation*.—Indistinguishable from foliage.
- *Petiole*.—Not present.

Flower

Natural flowering season:. Plants planted during April through October begin flowering December through February, without a juvenility period in Kfar Hess, Israel. Plants flower continuously under short day conditions.

Days to flowering from rooted cutting: Short day photoperiodic conditions. No juvenility.

Inflorescence type: Terminal and axillary panicle.

Individual flower type: Single, rotate 5 petaled with an obconical shaped hypanthium. Flowers outwardly facing.

Persistent or self-cleaning: Self-Cleaning.

Rate of flower opening: 30 to 50 days from bud to fully opened flower.

Typical flowering stem length: Approximately 70 to 100 cm.

Typical flowering stems harvested per plant: 120-150.

Vase life of flowers: Two weeks. Approximately 45 to 60 days on the plant.

Bud:

- *Shape*.—Round.
- *Length*.—0.45 cm.
- *Diameter*.—0.45 cm.
- *Color*.—Near RHS Red-Purple 67A.
- *Texture*.—Glabrous.

Inflorescence size:

- *Diameter*.—Approximately 18 cm.
- *Length*.—Approximately 15 cm.

Flower size:

- *Diameter*.—1.9 cm.
- *Length*.—0.6 cm.

Corolla:

- *Petals*.—Arrangement: Rotate, not overlapping. Length: 0.45 cm. Diameter: 0.55 cm. Quantity: 5. Texture: Smooth upper and lower surfaces. Apex: Obtuse rounded. Base: Fused into a hypanthium.
- *Color*.—When opening: Upper surface: Near Red-purple 70D. Lower surface: Near Red-purple 79D. Fully opened: Upper surface: Near Red-purple 69A. Lower surface: Near Red-purple 69A. Aging: Upper surface: Near Red-purple 69B. Lower surface: Near Red-purple 69B.

Hypanthium:

- *Diameter*.—0.8 cm.
- *Length*.—0.3 cm.
- *Shape*.—Obconical.
- *Color*.—When opening: Upper surface: Near Red-purple 70A. Lower surface: Near Red-purple 70A. Fully opened: Upper surface: Near Red-purple 70A. Lower surface: Near Red-purple 70A. Aging: Upper surface: Near Red-purple 70A. Lower surface: Near Red-purple 70A.

Calyx/sepals:

- *Quantity per flower*.—Fused into a single conical shape.
- *Shape*.—Conic.
- *Length*.—0.3 cm.
- *Width*.—0.8 cm.

*Margin*.—Entire, incised approximately 2 mm.
*Texture*.—Smooth outer and inner surfaces.
*Color*.—Near RHS Green 138A.

Peduncle: Peduncle is the plant stem/lateral branch.

Pedicel:
*Length*.—0.8 cm.
*Diameter*.—0.1 cm.
*Color*.—Near RHS Yellow-Green 146D.

Fragrance: None.

Reproductive Organs

Stamens:
*Number*.—10.
*Filament length*.—1 mm.
*Filament color*.—Near Red 56D.

Anthers:
*Shape*.—Oval.
*Width*.—0.1 mm.
*Length*.—0.25-0.5 mm.
*Color*.—Near Red-Purple 70A.

Pollen: Not observed.

Pistil:
*Number*.—1.
*Length*.—0.5 cm.
*Style*.—Length: 0.49 cm. Color: Near Red-Purple 69D.
*Stigma*.—Shape: Round. Color: Near Red-Purple 69A.

Other Characteristics

Seeds and fruits: Single flower produces one fruit. When the fruit is fertile, it will produce 1 seed, occasionally 2 seeds. Fruit type is a nut, colored near Grey-Brown N199A, seed is unwinged colored approximately 1.5 mm, brown in color, too minute to accurately measure color with RHS chart.

Disease/pest resistance: Neither resistance nor susceptibility to the normal diseases and pests of *Chamelaucium* have been observed to date.

Temperature tolerance: From −2° C. to 35° C.

Drought tolerance: Very good tolerance for drought.

What is claimed is:

1. A new and distinct cultivar of *Chamelaucium* plant named 'EARLY NIR' as herein illustrated and described.

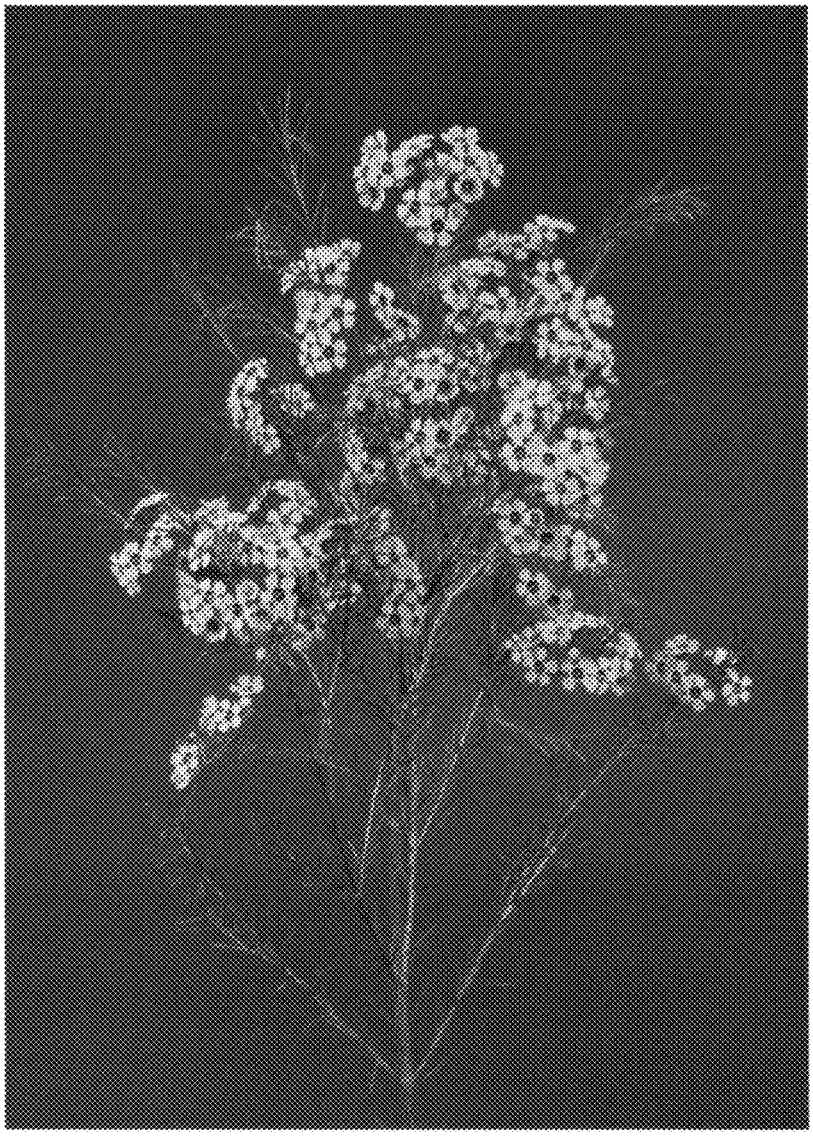

* * * * *